United States Patent
Serro

(10) Patent No.: US 7,227,168 B2
(45) Date of Patent: Jun. 5, 2007

(54) SYSTEM AND METHOD FOR READING OUT X-RAY INFORMATION STORED IN A PHOSPHOR LAYER

(75) Inventor: Hannes Serro, Munich (DE)

(73) Assignee: Agfa-Gevaert Healthcare GmbH, Leverkusen (DE)

(*) Notice: Subject to any disclaimer, the term of this patent is extended or adjusted under 35 U.S.C. 154(b) by 0 days.

(21) Appl. No.: 11/299,413

(22) Filed: Dec. 12, 2005

(65) Prior Publication Data
US 2006/0131524 A1 Jun. 22, 2006

(30) Foreign Application Priority Data
Dec. 20, 2004 (EP) .................. 04106745

(51) Int. Cl.
*G03B 42/08* (2006.01)
(52) U.S. Cl. ..................... 250/584; 250/587
(58) Field of Classification Search .............. 250/584, 250/580, 581, 582, 583
See application file for complete search history.

(56) References Cited

U.S. PATENT DOCUMENTS

| 4,739,480 A | * | 4/1988 | Oono et al. | 250/584 |
| 6,229,910 B1 | * | 5/2001 | Kaneko | 382/128 |
| 6,373,074 B1 | | 4/2002 | Mueller et al. | |
| 6,501,088 B1 | | 12/2002 | Struye et al. | |
| 6,542,579 B1 | | 4/2003 | Takasawa | |
| 7,054,472 B1 | * | 5/2006 | Funahashi | 382/128 |
| 7,095,034 B2 | * | 8/2006 | Haug et al. | 250/484.4 |
| 2003/0142119 A1 | | 7/2003 | Akagi | |

FOREIGN PATENT DOCUMENTS

| DE | 10255958 | 6/2004 |
| EP | 1103219 | 5/2001 |
| EP | 1415594 | 5/2004 |

* cited by examiner

*Primary Examiner*—David Porta
*Assistant Examiner*—Faye Boosalis
(74) *Attorney, Agent, or Firm*—Houston Eliseeva LLP

(57) ABSTRACT

A system and corresponding method for reading out X-ray information stored in a phosphor layer, includes a read-out device for reading out the X-ray information stored in the phosphor layer, and an input unit integrated in to the read-out device for entering additional information by an operator where the input unit is in the form of a graphical input unit into which the additional information can be entered in graphical form by the operator. Moreover, an allocation device is provided for allocating the entered additional information in graphical form to the X-ray information read out.

18 Claims, 2 Drawing Sheets

SYSTEM AND METHOD FOR READING OUT X-RAY INFORMATION STORED IN A PHOSPHOR LAYER

The invention relates to a system and to a corresponding method for reading out X-ray information stored in a phosphor layer.

BACKGROUND OF THE INVENTION

One possibility for recording X-ray pictures includes storing the X-ray radiation passing through an object, for example a patient, as a latent picture in a phosphor layer. In order to read out the latent picture, the phosphor layer is irradiated with stimulation light, and so stimulated into emitting emission light. The emission light, the intensity of which corresponds to the picture stored in the phosphor layer, is collected by an optical detector and converted into electrical signals. The electrical signals are further processed as required, and finally made available for analysis, in particular for medical/diagnostic purposes, when they are displayed on an appropriate display unit, such as a monitor or printer.

In known systems and methods, before and/or after an X-ray is taken, additional information on the identity of the patient, the X-ray, the subsequent read-out of the latent picture and/or processing of the X-ray information read out are entered into a data input station, a so-called ID station.

In certain applications, in particular with emergency cases, time delays in entering additional information should be avoided as much as possible. The systems and methods known from the prior art are therefore only suitable to a certain extent for such applications.

SUMMARY OF THE INVENTION

It is an object of the invention to provide a system and a corresponding method for reading out X-ray information stored in a phosphor layer, with which additional information can be entered in the simplest and quickest way possible.

The above and others objects are fulfilled by a system and corresponding method for reading out X-ray information stored in a phosphor layer, includes a read-out device for reading out the X-ray information stored in the phosphor layer, and an input unit integrated in to the read-out device for entering additional information by an operator where the input unit is in the form of a graphical input unit into which the additional information can be entered in graphical form by the operator. Moreover, an allocation device is provided for allocating the entered additional information in graphical form to the X-ray information read out.

Allocation in the sense of the present invention means that the additional information in graphic form is assigned to or correlated with the read-out X-ray information. For example, the entered additional information which relates to the X-ray information of a patient, is stored together with the X-ray information of the patient, e.g. under the name and/or ID number of this patient.

By using a graphic input unit, simpler and quicker input of additional information is made possible in comparison to conventional data input by means of a keyboard. The system and method according to the invention are therefore particularly advantageous with the radiological diagnosis of emergency patients. Moreover, the graphic additional information can be input in any form and with any content, and is not restricted to specific data fields or data formats. In this way, additional information, such as sketches or any form of symbol, can be allocated to the X-ray information read out which can not be taken into consideration when entering data in systems known from the prior art. In particular, the orientation of a patient at the time when a latent image of the patient is recorded in the phosphor layer can be entered easily by an operator.

Furthermore, by integrating the input unit into the read-out device it is possible for the graphic additional information to be entered by an operator when the latter is in the vicinity of the read-out device, in particular when inserting or removing the cassette which holds the storage phosphor layer to be read out. In this way, a separate walk to a data input station, for example an ID station, becomes superfluous, and instead the data can be entered immediately at the read-out device.

Integration of the input unit in the sense of the invention means that the read-out device includes a housing, and the input unit is accommodated within this housing or forms a component part of this housing.

In a preferred embodiment, provision is made such that the input unit is designed for the hand-written input of additional information by the operator, in particular in the form of text, pictures or symbols. Hand-written input is a particularly simple and direct possibility for entering additional information. For example, in this way the operator can also provide a hand-written signature, e.g. in the form of a full signature or an abbreviated name.

Preferably, the input unit is designed as a touch-sensitive input unit into which the additional information can be entered by touching the input unit, in particular by writing or drawing movements on the input unit. The input can be realised either by the operator's finger or hand or by making use of an appropriate input pen.

Preferably, a display unit is provided which is designed to display the additional information when it is entered. The display unit here can either be disposed separately from the input unit or be integrated into the same in a combined display and input unit. This type of combined display and input unit is also called a touch screen or touch panel. This has the advantage that the operator can immediately check the additional information when it is entered.

The display and input unit can additionally be designed to show pictograms which symbolise different operation modes of the read-out device and/or the input unit, and which can be selected by touching the input unit in the region of the pictograms shown. Touching here can also be by means of a finger and/or an input pen. In this way, in addition the control of the read-out device and the menu control in the display and input unit are simplified.

In a variation of the invention, a conversion device is provided for converting the additional information from the graphic form into a symbol-orientated form, and the allocation device is designed for allocating the additional information in the symbol-orientated form to the X-ray information read out. The conversion device here preferably converts the handwritten symbols entered into alpha-numerical symbol sequences which are there then allocated to the X-ray information read out. By converting the graphic additional information into a symbol-orientated form, the storage space requirement for the storage of additional information is reduced.

Preferably, the X-ray information read out is presented together with the graphic additional information entered. It is presented in particular on a monitor or a hard copy. The additional information entered is thus available together with the X-ray information presented, and can be used directly for interpreting or analysing the same, or for other purposes. This is particularly advantageous for the diagnosis of emergency patients with which, as well as fast input of the additional information, presentation which gives the best possible overview of the additional information available is required.

BRIEF DESCRIPTION OF THE DRAWINGS

Additional features and advantages of the invention are given in the following description of preferred embodiments and examples of applications, reference being made to the attached drawings.

DETAILED DESCRIPTION OF THE PREFERRED EMBODIMENTS

Figure 1:
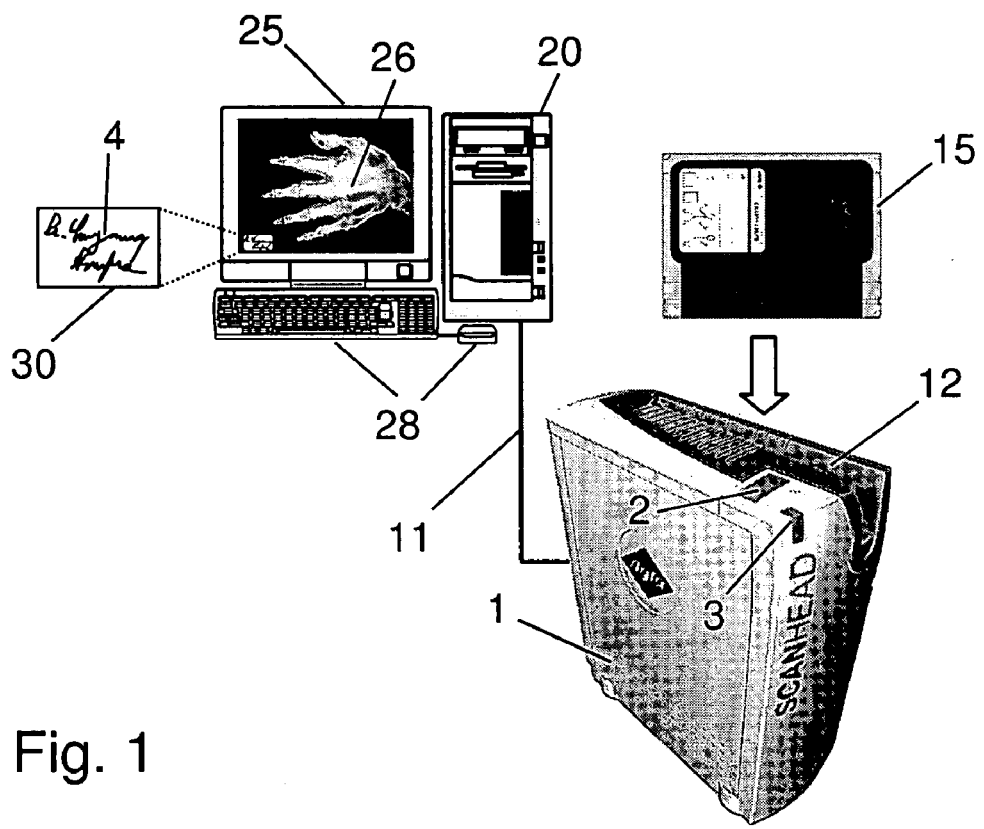
FIG. 1 shows one embodiment of a system according to the invention.

FIG. 1 shows an example of an embodiment of the system according to the invention which comprises a read-out device 1 for reading out X-ray information from a phosphor layer.

Before the read-out, a cassette 15, in which a phosphor layer is located, is inserted into a cassette holder 12 of the read-out device 1. In this position the cassette 15 is opened, and the phosphor layer (also referred to as a "storage phosphor layer") located within it is removed and conveyed into the inside of the read-out device 1. Here, the phosphor layer is read out.

For the read-out, a so-called line scanner is preferably provided with which one whole line of the storage phosphor layer is respectively irradiated with stimulation light, and the emission light produced here is collected with a linear detector array. Details on the structure of this type of line scanner can be taken for example from U.S. Pat. No. 6,373,074. Alternatively, a so-called flying spot scanner can also be used here, as described for example in U.S. Pat. No. 6,501,088. Both U.S. Pat. Nos. 6,373,074 and 6,501,088 are herein incorporated by reference in their entirety for background information only After the read-out process, any residual information remaining in the phosphor layer is deleted by irradiating the phosphor layer with light of an appropriate spectral distribution and intensity. After deletion, the phosphor layer is conveyed back into the cassette 15, and can be removed by the operator and made ready for further X-rays.

The read-out device 1 has a status display 3 for displaying the respective operational state. If for example the status display 3 is illuminated or flashing green, this signals that the read-out device 1 is ready for use or is temporarily busy reading out and deleting a phosphor layer. If on the other hand the status display 3 is illuminated or flashing red, this signals the presence of a fault or the implementation of a start or self-testing programme.

As well as the status display 3, the read-out device 1 has an input unit 2 by means of which additional information can be entered by the operator. The input unit 2 is designed here according to the invention as a graphic input unit so that the additional information can be entered by the operator in graphic form. Preferably, the additional information is entered here directly before or after the read-out or during the read-out of the phosphor layer in the read-out device 1.

According to the invention, the additional information entered is allocated to the respective X-ray information read out. This preferably happens by transferring both the X-ray information read out and the additional information entered via a data line 11 to a computer system 20 in which a storage unit is provided for storing this information.

The allocation of the additional information to the respective X-ray information can take place for example by storing the additional information and the associated X-ray information in a common data field in the storage unit of the computer system 20. Alternatively or in addition, both types of information can however also be stored in different data fields, allocation being achieved for example by means of appropriate address pointers.

Furthermore, the system according to the invention has a monitor 25 on which the X-ray information read out is presented in the form of an X-ray picture 26 together with the additional information 4 entered. In the example shown, the additional information 4 is reproduced in a special presentation field 30 in the lower left-hand region of the X-ray picture 26 shown. In order to improve the clarity, the presentation field 30 and the additional information 4 shown therein are additionally shown enlarged. The size and arrangement of the presentation field 30 for the additional information 4 entered in the X-ray picture 26 can be changed in any way by the operator by means of appropriate operating elements 28, such as a keyboard and/or a computer mouse.

Figure 2:
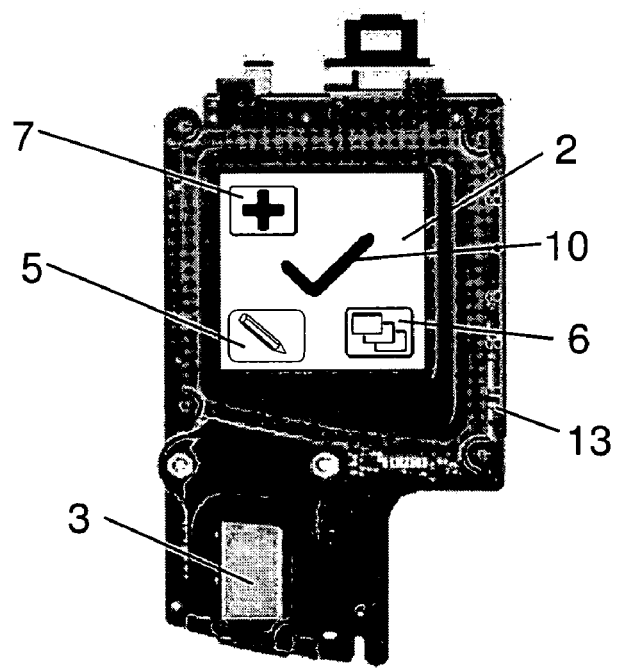
FIG. 2 shows one embodiment of an input unit.

FIG. 2 shows an example of an embodiment of an input unit 2 which, together with the status display 3, is disposed on a plate 13. By combining the two components on one plate 13, the integration both of the input unit 2 and the status display 3 into the housing of the read-out device 1 and the technical wiring realisation are simplified.

In the example shown, the input unit 2 is combined with a display unit, and together with this forms a display and input unit which is also called a touch screen or touch panel.

In the region of the input unit 2, different pictograms 5, 6 and 7 and a symbol 10 are displayed in the display unit. By touching the input unit 2 in the region of a pictogram 5, 6 or 7, the function allocated to the respective pictogram 5, 6 or 7 is selected and implemented.

By touching the input unit 2 in the region of the first pictogram 7, an operation mode is selected in which the phosphor layer located in the cassette 15 can be immediately entered into the read-out device 1 and read out, without previously or subsequently requiring the input of data on the patient, the X-ray and/or further processing of the X-ray information read out. This operation mode is also called an Emergency Case because it is used in particular in emergency cases where there is no time for entering the aforementioned data.

By actuating the second pictogram 6, an overview of further functions or operation modes of the input device 2 and/or the read-out device 1 can be accessed.

By selecting the third pictogram 5, the input unit 2 is shifted into a graphic input mode in which the operator can enter additional information in graphic form.

The symbol 10 shown in the form of a tick shows the general operational readiness of the read-out device 1.

The active display area of the input unit 2 has side dimensions which are typically between 50 and 100 mm.

The number of pixels is typically between 20,000 and 100,000. Typical dimensions of a pixel fall within the range of between 0.2 and 0.5 mm. In the example shown in FIG. 2, the active display area is 56×56 mm, the individual pixels covering an area of 0.35×0.35 mm. Overall, the active display area thus comprises 160×160=25,600 pixels. A touch-sensitive region of the input unit 2 is allocated to each pixel of the display unit.

Figure 3:
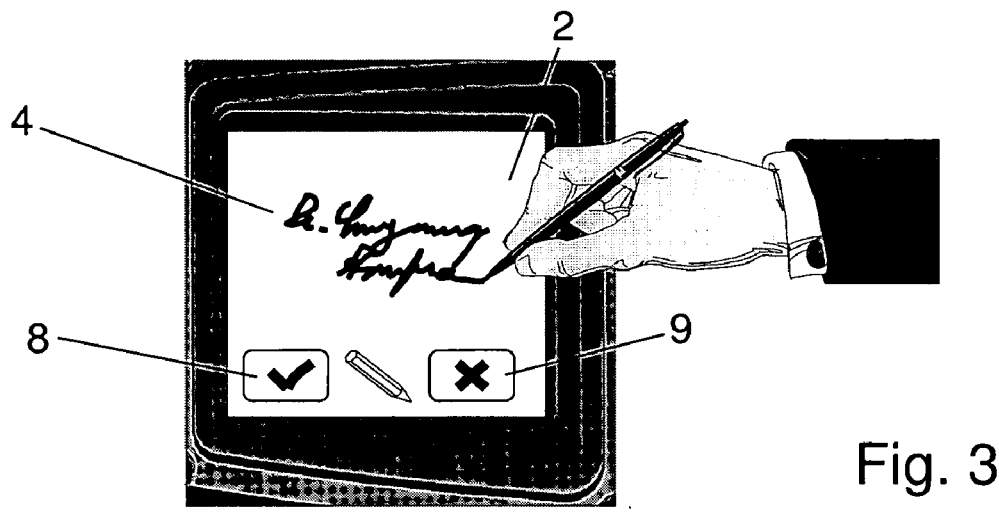
FIG. 3 shows a first example of entering graphic information.
Figure 4:
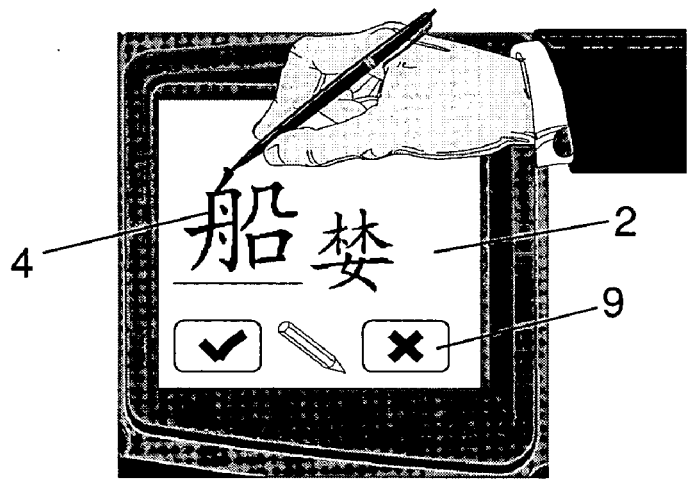
FIG. 4 shows a second example of entering graphic information.
Figure 5:
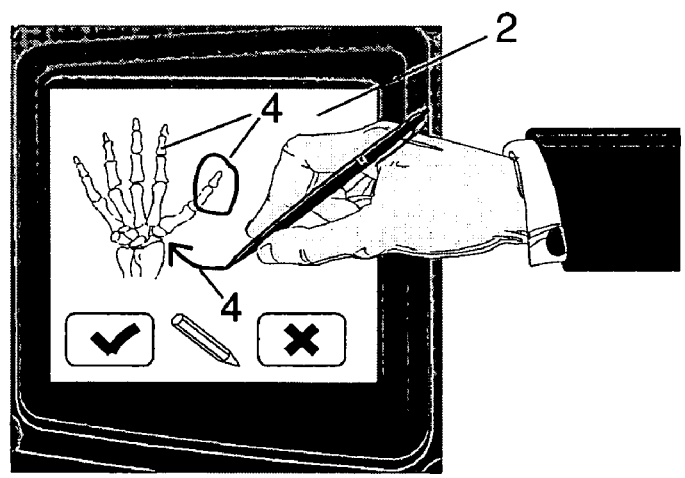
FIG. 5 shows a third example of entering graphic information.

FIGS. 3 to 5 show examples of entering graphic information by means of the input unit 2 while the latter is in graphic input mode.

In FIG. 3 the additional information 4 is entered in the form of a hand-written text or a signature. The input is implemented here, as shown, by making use of an input pen.

By touching a fourth pictogram 9, the currently entered graphic additional information can be deleted again and if required, re-entered.

By touching the fifth pictogram 8, the input mode is ended. The display of the input unit 2 is then reset in the state shown in FIG. 2. The graphic additional information entered can now be stored together with the X-ray information read out, preferably in a storage unit of the computer system 20 (see FIG. 1).

As shown by the second example illustrated in FIG. 4, the graphic additional information 4 can also be provided in the form of any national character and/or symbols. The display and input unit is preferably provided with a function in which the pictograms, symbols or text information displayed are reconfigured in any way and so can be adapted to particular applications or the respective national language. The fourth pictogram 9 can thus for example be changed into a corresponding Asian character for "delete".

As shown by the third example in FIG. 5, the additional information 4 entered can also be in the form of a picture and/or in the form of symbols or accentuations of a respectively displayed picture.

With the examples of embodiments shown, the graphic input unit 2 is operated such that it serves both for the simple control of the read-out device 1 and/or the input unit 2 by touching pictograms and for the simple and fast handwritten input of graphic additional information. In this way it is particularly suitable for the radiological diagnosis of emergency patients.

The invention claimed is:

1. A system for reading out X-ray information stored in a phosphor layer, comprising:
 a read-out device for reading out the X-ray information stored in the phosphor layer;
 an input unit for the entering of additional information by an operator;
 wherein
 the input unit is integrated into the read-out device,
 the input unit is in the form of a graphic input unit into which the additional information can be entered in graphic form by the operator,
 an allocation device is provided for allocating the entered additional information in graphic form to the X-ray information read out,
 the input unit is capable of accepting hand-written input of the additional information, including in the form of text, pictures, symbols or a signature.

2. The system according to claim 1, wherein the input unit is a touch-sensitive input unit into which the additional information can be entered by touching the input unit, including by writing or drawing movements on the input unit, and a display unit is provided for displaying the additional information when entered, and wherein the display unit and the input unit are integrated in a combination display and input unit which is in the form of a touch screen.

3. The system according to claim 2, wherein the combination unit can present pictograms which symbolise different operational modes of the read-out device and of the combination unit and which can be selected by touching the combination unit.

4. The system according to claim 2, further comprising a presentation device, including a monitor or a printer being provided in order to present the X-ray information read out together with the additional information entered.

5. The system according to claim 1, wherein the input unit is a touch-sensitive input unit into which the additional information can be entered by touching the input unit, including by writing or drawing movements on the input unit, and a display unit is provided for displaying the additional information when entered, and wherein the display unit and the input unit are integrated in a combination display and input unit which is in the form of a touch screen.

6. The system according to claim 2, wherein the combination unit can present pictograms which symbolise different operational modes of the read-out device or of the combination unit and which can be selected by touching the combination unit.

7. The system according to claim 1, further comprising a presentation device, including a monitor or a printer being provided in order to present the X-ray information read out together with the additional information entered.

8. The system according to claim 1, further comprising a presentation device, including a monitor or a printer being provided in order to present the X-ray information read out together with the additional information entered.

9. A method for reading out X-ray information stored in a phosphor layer with the following steps:
 entering additional information into an input unit by an operator in graphic form, the additional information being entered into the input unit in handwriting;
 reading out the X-ray information stored in the phosphor layer; and
 allocating the additional information entered into the input unit in handwriting in graphic form to the X-ray information read out.

10. The method according to claim 9, wherein the additional information is entered in the form of hand-written text or hand-produced pictures, symbols or a signature.

11. The method according to claim 10, wherein the additional information is entered by touching the input unit, including by writing or drawing movements on the input unit, and the additional information is displayed when entered.

12. The method according to claim 10, wherein pictograms are displayed and selected by touching the input unit, said pictograms symbolizing different operational modes of the read-out device and the input unit.

13. The method according to claim 10, wherein pictograms are displayed and selected by touching the input unit, said pictograms symbolizing different operational modes of the read-out device or the input unit.

14. The method according to claim 9, wherein the additional information is entered by touching the input unit, including by writing or drawing movements on the input unit, and the additional information is displayed when entered.

15. The method according to claim 9, wherein pictograms are displayed and selected by touching the input unit, said pictograms symbolizing different operational modes of the read-out device and the input unit.

16. The method according to claim 13, wherein at least one of the pictograms is formed using the additional information entered into the input unit.

17. The method according to claim 9, wherein the entered additional information is presented, on a monitor or as a hard copy by a printer, in graphic form together with the X-ray information read out.

18. The method according to claim 9, wherein pictograms are displayed and selected by touching the input unit, said pictograms symbolizing different operational modes of the read-out device or the input unit.

* * * * *